(12) United States Patent
Phillips

(10) Patent No.: US 7,789,835 B2
(45) Date of Patent: Sep. 7, 2010

(54) METHODS AND SYSTEMS FOR DETERMINING CARDIAC OUTPUT BASED ON A VALVE CROSS SECTIONAL AREA ESTIMATE

(75) Inventor: Robert Allan Phillips, Coffs Harbour (AU)

(73) Assignee: Uscom Limited, Sydney (AU)

( * ) Notice: Subject to any disclaimer, the term of this patent is extended or adjusted under 35 U.S.C. 154(b) by 477 days.

(21) Appl. No.: 10/761,899

(22) Filed: Jan. 21, 2004

(65) Prior Publication Data

US 2004/0171949 A1    Sep. 2, 2004

(30) Foreign Application Priority Data

Jan. 22, 2003    (AU) .............................. 2003900261

(51) Int. Cl.
 *A61B 5/00* (2006.01)
(52) U.S. Cl. ....................................... 600/454; 600/508
(58) Field of Classification Search ...................... None
See application file for complete search history.

(56) References Cited

U.S. PATENT DOCUMENTS

| | | | |
|---|---|---|---|
| 3,675,640 A | 7/1972 | Gatts | |
| 3,980,075 A | 9/1976 | Heule | |
| 4,413,629 A | 11/1983 | Durley, III | |
| 4,509,526 A * | 4/1985 | Barnes et al. | 600/456 |
| 4,671,295 A | 6/1987 | Abrams et al. | |
| 4,796,634 A * | 1/1989 | Huntsman et al. | 600/457 |
| 4,807,636 A | 2/1989 | Skidmore et al. | |
| 4,858,614 A * | 8/1989 | Stevens et al. | 600/543 |
| 4,866,613 A | 9/1989 | Amemiya et al. | |
| 4,867,165 A | 9/1989 | Noller et al. | |
| 5,020,516 A | 6/1991 | Biondi et al. | |
| 5,052,395 A | 10/1991 | Burton et al. | |
| 5,086,776 A | 2/1992 | Fowler, Jr. et al. | |
| 5,139,020 A | 8/1992 | Koestner et al. | |
| 5,152,291 A | 10/1992 | Dias | |
| 5,183,040 A | 2/1993 | Nappholz et al. | |
| 5,188,106 A | 2/1993 | Nappholz et al. | |
| 5,241,966 A * | 9/1993 | Finkelstein et al. | 600/485 |
| 5,265,615 A | 11/1993 | Frank et al. | |
| 5,313,947 A | 5/1994 | Micco | |

(Continued)

FOREIGN PATENT DOCUMENTS

DE     40 20 519 A1    1/1995

(Continued)

OTHER PUBLICATIONS

Foale et al., Echocardiographic measurement of the normal adult right ventricle, Br Heart J 1986; 56: 33-44.*

(Continued)

*Primary Examiner*—Carl H Layno
*Assistant Examiner*—Yun Haeng Lee
(74) *Attorney, Agent, or Firm*—Merchant & Gould P.C.

(57) ABSTRACT

Described herein are systems and methods for determining the cardiac output of a patient. One such method includes measuring the patient's height and the velocity time integral or stroke distance of blood flowing from the heart of the patient, and subsequently utilising these measurements to determine the cardiac output of the patient based on a valve cross sectional area estimate.

5 Claims, 4 Drawing Sheets

U.S. PATENT DOCUMENTS

| | | |
|---|---|---|
| 5,361,771 A | 11/1994 | Craine et al. |
| 5,389,217 A | 2/1995 | Singer |
| 5,447,164 A | 9/1995 | Shaya et al. |
| 5,546,943 A | 8/1996 | Gould |
| 5,584,298 A | 12/1996 | Kabal |
| 5,634,467 A | 6/1997 | Nevo |
| 5,640,960 A | 6/1997 | Jones et al. |
| 5,891,036 A | 4/1999 | Izumi |
| 6,106,472 A | 8/2000 | Chiang et al. |
| 6,149,587 A | 11/2000 | Raines |
| 6,217,522 B1 | 4/2001 | Shoshan |
| 6,234,963 B1 | 5/2001 | Blike et al. |
| 6,285,898 B1 | 9/2001 | Ben-Haim |
| 6,292,689 B1 | 9/2001 | Wallace et al. |
| 6,315,730 B1 | 11/2001 | Hoff et al. |
| 6,468,219 B1 | 10/2002 | Njemanze |
| 6,506,157 B1 | 1/2003 | Teigman et al. |
| 6,511,413 B2 | 1/2003 | Landesberg |
| 6,522,923 B1 | 2/2003 | Turcott |
| 6,527,722 B1 | 3/2003 | Fazioli et al. |
| 6,530,887 B1 | 3/2003 | Gilbert et al. |
| 6,565,513 B1 | 5/2003 | Phillips |
| 6,569,101 B2 | 5/2003 | Quistgaard et al. |
| 6,577,901 B2 | 6/2003 | Thompson |
| 6,580,946 B2 | 6/2003 | Struble |
| 6,685,621 B2 | 2/2004 | Bolling et al. |
| 6,776,764 B2 | 8/2004 | Pinsky |
| 7,024,244 B2 | 4/2006 | Muhlenberg et al. |
| 7,144,365 B2 | 12/2006 | Bolling et al. |
| 7,192,403 B2 | 3/2007 | Russell |
| 2002/0091319 A1 | 7/2002 | Moehring et al. |
| 2002/0138512 A1 | 9/2002 | Buresh et al. |
| 2003/0100925 A1 | 5/2003 | Pape et al. |
| 2003/0163056 A1* | 8/2003 | Osypka et al. ............. 600/504 |
| 2003/0195409 A1* | 10/2003 | Seitz et al. ................ 600/407 |
| 2003/0199779 A1* | 10/2003 | Muhlenberg et al. ........ 600/513 |
| 2004/0254483 A1 | 12/2004 | Zdeblick et al. |

FOREIGN PATENT DOCUMENTS

| | | |
|---|---|---|
| EP | 0 420 085 | 4/1991 |
| EP | 0 474 957 | 3/1992 |
| EP | 0 503 285 | 9/1992 |
| EP | 0 706 777 | 4/1996 |
| EP | 1 103 217 A2 | 5/2001 |
| EP | 1 250 889 | 10/2002 |
| EP | 1 304 074 A2 | 4/2003 |
| GB | 1 461 345 | 1/1977 |
| WO | WO 89/04634 | 6/1989 |
| WO | 92/06633 | 4/1992 |
| WO | WO 95/19806 | 7/1995 |
| WO | 96/01586 | 1/1996 |
| WO | WO 96/32888 | 10/1996 |
| WO | WO 97/12547 | 4/1997 |
| WO | 99/66835 | 12/1999 |
| WO | WO 99/66835 | 12/1999 |
| WO | WO 00/62858 | 10/2000 |
| WO | WO 01/48451 | 7/2001 |
| WO | WO 03/015609 | 2/2003 |

OTHER PUBLICATIONS

Nidorf et al. "New perspectives in the Assessment of Cardiac Chamber Dimensions During Development and Adulthood." *JACC* vol. 19, No. 5. Apr. 1992. pp. 983-988.

Devereux et al., American Journal of Hypertension—Abstract of Article: "Relations of Doppler Stroke Volume and Its Components to Left Ventricular Stroke Volume in Normotensive and Hypertensive American Indians", www.nature.com/ajh/journal /v10/n6/abs/ajh1997807a.html, 1997 2 pages.

Quinones et al., "American Society of Echocardiography Report: Recommendations for Quantification of Doppler Echocardiography: A Report From the Doppler Quantification Task Force of the Nomenclature and Standards Committee of the American Society of Echocardiography", Journal of the American Society of Echocardiography, vol. 15, No. 2, Feb. 2002, pp. 167-184.

\* cited by examiner

METHODS AND SYSTEMS FOR DETERMINING CARDIAC OUTPUT BASED ON A VALVE CROSS SECTIONAL AREA ESTIMATE

FIELD OF THE INVENTION

The present invention relates to the measurement of blood flow in the body and, in particular, to the measurement of cardiac output from the heart.

BACKGROUND OF THE INVENTION

Cardiac output and measurement of cardiac dimensions and haemodynamics are very important indicators in measuring health or detecting disease. The cardiac output, the volume of blood ejected by the heart per minute, is an essential measure of cardiac health.

Unfortunately, it is often difficult to measure actual cardiac output. Whilst normal fluid flow outputs consist of a flow velocity times a cross section area, it is often difficult to accurately measure the cross sectional area of cardiac vessels. Hence, there is often a large degree of error associated with actual cardiac measurements.

SUMMARY OF THE INVENTION

It is an object of the present invention to provide for an improved or alternative way for measurement of cardiac output.

In accordance with a first aspect of the present invention, there is provided a method of determining the cardiac output of a patient, the method comprising the steps of: (a) measuring the patients height; (b) measuring the velocity time integral or stroke distance of blood flowing from the heart of the patient, (c) utilising the two measurements in step (a) and (b) to determine the cardiac output of the patient.

Preferably the method also includes the step of measuring the correlation between the patient's height and cross sectional area of a cardiac valve of a population of individuals and utilising the correlation in step (c) to determine the cardiac output of the patient. The population can be selected having similar body characteristics to the patient.

The step (c) can comprise utilising the formula substantially of the form: aortic annular diameter=0.010×height (cms)+0.25 cm to determining the diameter of the aortic annular and then determining a cross sectional.

The step (c) can comprise utilising the formula substantially of the form: pulmonary annular diameter=0.0106× height (cms)+0.265 cm to determine the diameter of the pulmonary valve and then determining a cross sectional area.

BRIEF DESCRIPTION OF THE DRAWINGS

The preferred embodiments of the present invention will now be described with reference to the accompanying drawings in which.

DESCRIPTION OF PREFERRED AND OTHER EMBODIMENTS

In the preferred embodiment, a new method is provided for measurement of cardiac output through the utilisation of correlations between height measurements and integrated transvalvular haemodynamics.

Recently, in PCT application No. PCT/AU99/00507 and U.S. Pat. No. 6,565,513 entitled "Ultrasonic Cardiac Output Monitor" the contents of which are hereby incorporated by cross reference, a system was proposed for the continuous wave Doppler direct measurement of transvalvular cardiac flows. Such a system can readily be adapted for use with the preferred embodiment of the present invention to measure flow outputs.

Figure 1:
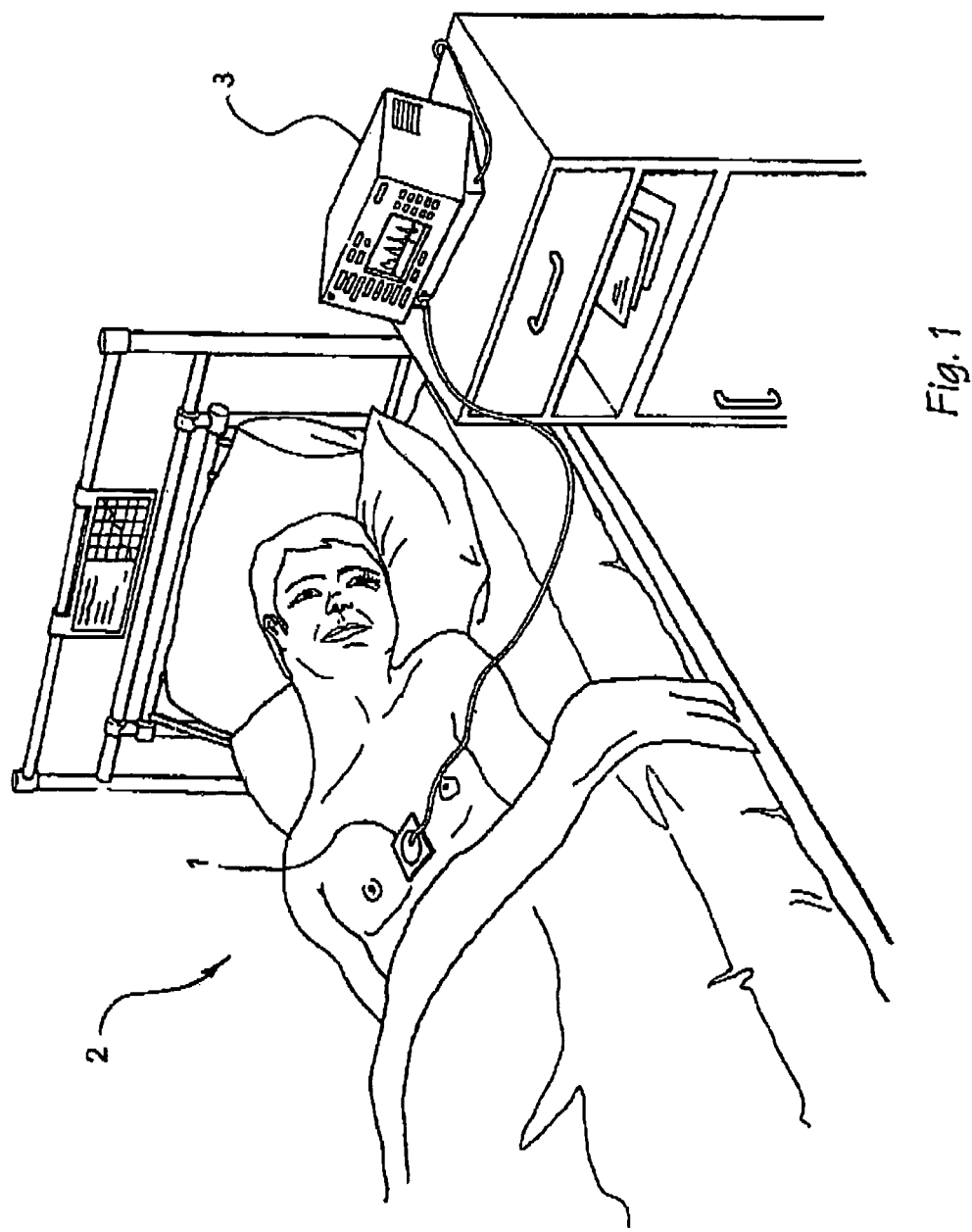
FIG. 1 is a side perspective view of a cardiac monitoring system.

FIG. 1 illustrates the system described in the aforementioned patent specification wherein an ultrasonic transducer device 1 is interconnected to a small processing computer 3 and utilised to monitor blood flows within the heart of patient 2.

Figure 2:
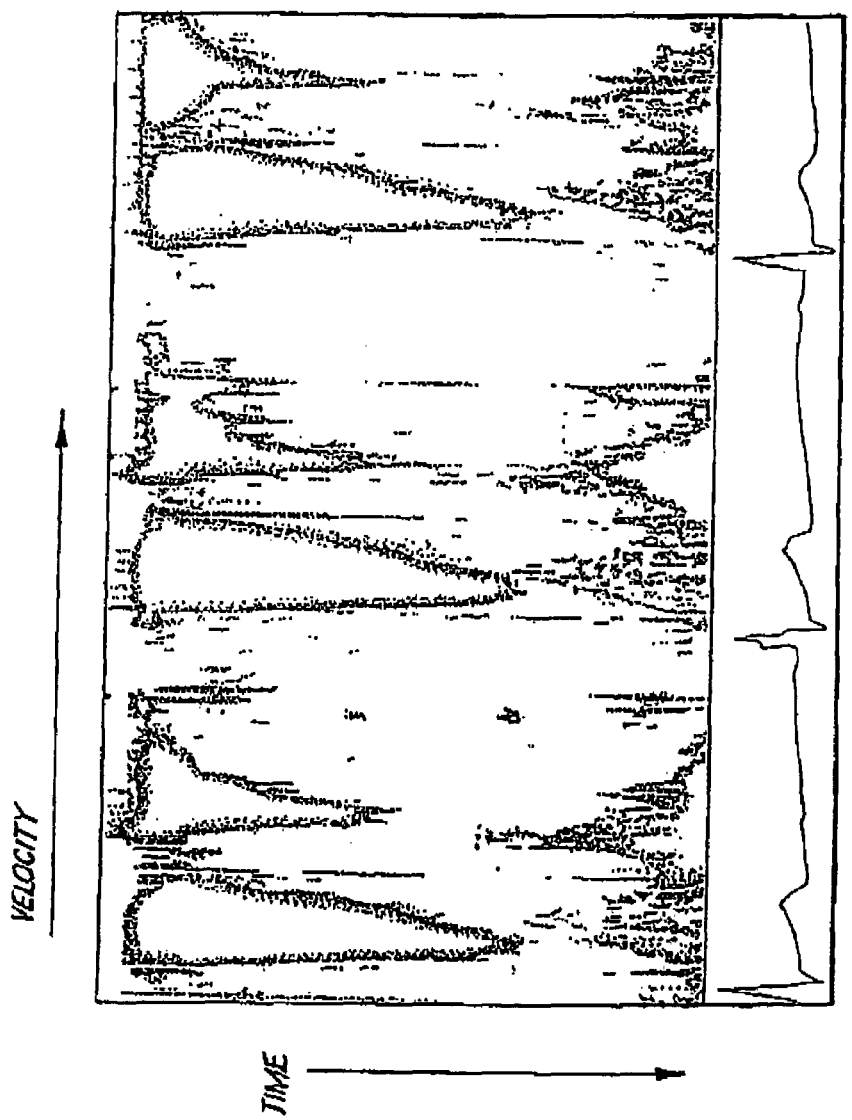
FIG. 2 and FIG. 3 illustrate screen dumps of CW ultrasound type devices.
Figure 3:
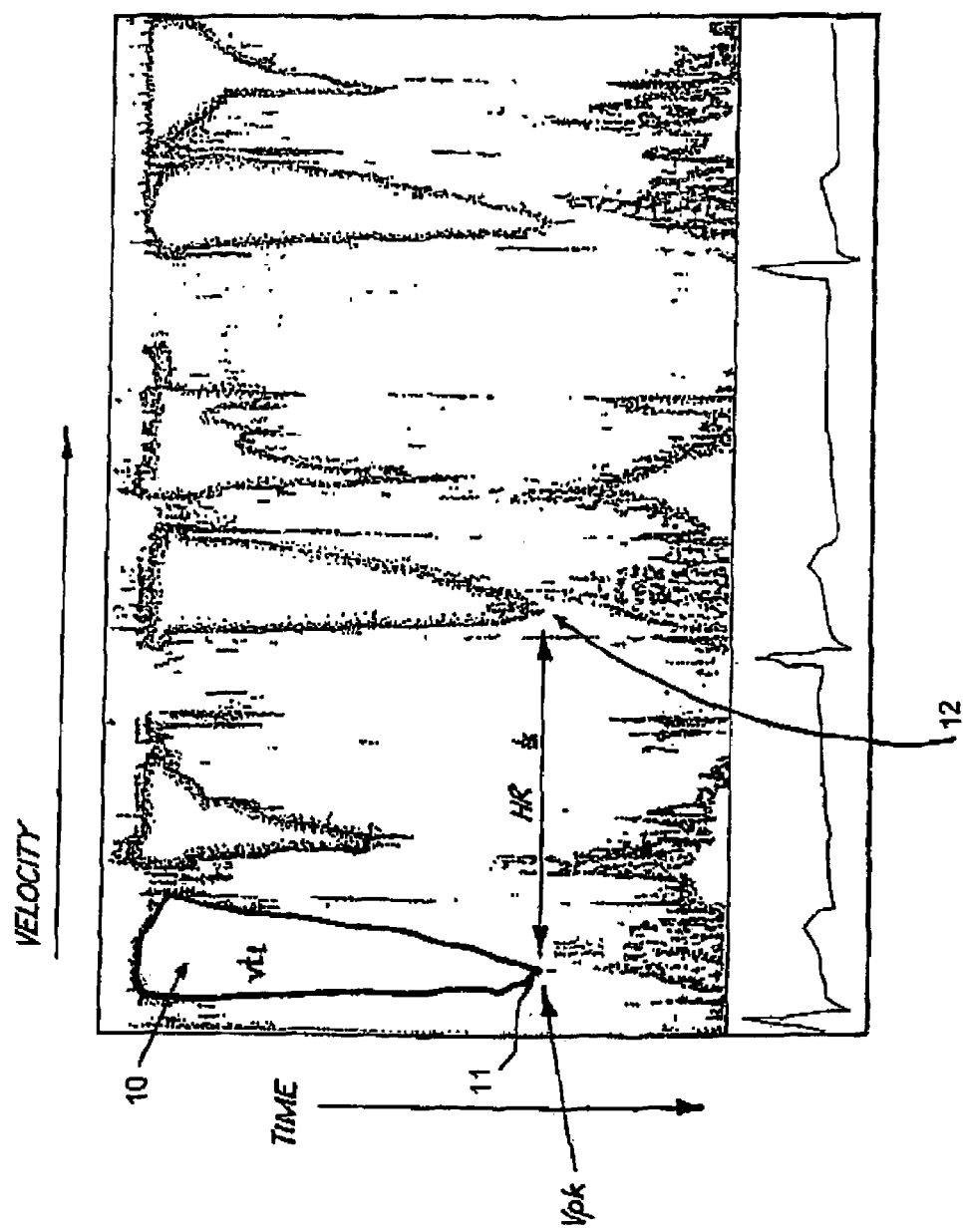

Turning to FIG. 2, there is illustrated a screen dump from an ultrasonic transducer device being placed in accordance with the teaching of the aforementioned application so as to measure transvalvular flows. In FIG. 3, there is illustrated an analysis of the image of FIG. 2. With such an output, cardiac output (CO) can be calculated by measurement of the Doppler spectral flow profile of the image of FIG. 2 to determine the area under the curve or the velocity time integral (vti) or stroke distance—the distance a single red blood cell travels per beat. In FIG. 3, there is illustrated the vti 10 which is an "area under the curve" measurement. Further, the heart rate can be determining from the spectral flow profile as the time between peaks e.g. 11, 12.

From a measurement of the cross sectional area of the flow (XSA), it is possible to determine the stroke volume (SV) by multiplying the vti so that SV=vti×XSA. SV is the volume of blood ejected by the heart per beat in $cm^3$. CO is a function of SV and heart rate (HR), or the volume per beat times the number of beats per minute, so CO=SV×HR in liters per minute.

The values for these formulae can be derived from direct measurement of the Doppler flow profile of FIG. 2 and FIG. 3, with the exception of the flow cross sectional area.

One possibility for measuring the flow cross-sectional area is to measure the flow diameter using two-dimensional ultrasound, and calculating the XSA using $\pi r^2$. However, normal values for flow diameters obtained are in the order f1.5 to 2.5 cm. The resolution of 2D B-Mode ultrasound at 3 Mhz is approximately 1 mm or about 5%. This 5% linear error is the best possible result and, if 95% confidence intervals define sensitivity and equal two standard deviations then the error is approximately 10%. If this error is squared when applied to the $\pi r^2$ formula to determine XSA, the resulting potential error in measurement of the cardiac output is approximately 21%.

It will be noted that the error associated with measurement of the Doppler functions alone for application of these haemodynamics equations is less than 5%. The figures for sensitivity of Doppler echo detection of changes in CO are reflected in clinical data.

In the preferred embodiment, a more accurate method of measuring flow diameter is utilised to provide an increase in the sensitivity of Doppler ultrasound to detection of changes in cardiac output and to hereby improve the clinical usefulness of Doppler flow measurements.

CO measurements are generally made from Doppler flow profiles across the aortic and pulmonary valves. However, it is also possible to determine CO from the flow across the mitral and tricuspid valves. Measurement of Aortic annular diameter, the two dimensional measure from which the XSA is derived, can generally be performed with reasonable accuracy because the arterial walls are normally perpendicular to insonation in the parasternal long axis position, resulting in high levels of reflected signals. Measurement of the pulmonary annular diameter is more problematic because the vessel walls am often parallel to the ultrasound beam and reflected signal less intense. Of additional importance, the pulmonary artery is the most accessible flow signal for Doppler measurement of CO.

Recently, Nidorf et al (Nidorf S M, Picard M H, Triulzi M O, Thomas J D, Newell J, King, M E, Weyman A E, "New perspectives in the assessment of cardiac chamber dimensions during development and adulthood". J Am Coll Cardiac 1992; 19:983-8) in a study of 268 normal persons aged 6 days to 76 yrs, there was presented information that height was a significant predictor of the cardiac linear dimensions.

Regression coefficients included aortic annular diameter (r=0.96), Left atrial size (r=0.91), LVDd(r=0.94) and LV length (r=0.93). Further, this study found that the heart and great vessels grew in unison and at a predictable rate after birth reaching 50% of their adult dimensions at birth, 75% at 5 yrs and 90% at 12 yrs.

Height has the additional benefits of being a non-derived unit, is easily measured, and is a commonly patient informed value. Through subsequent analysis, it has been found that the size of the aortic annular diameter can be approximately described by the regression equation as 0.010×height (cms)+ 0.25 cms. If the heart grows in unison and at a predictable rate, then the pulmonary artery annular diameter will show constant a relationship to the aortic annulus at any age. Hence, the Cardiac Output can be predicted using the aortic annular diameter regression equation and integrated haemodynanics. As input CO equals output CO in the absence of shunt or significant regurgitation, a height referenced equation to predict the pulmonary artery annular diameter can also be utilised. This can then be applied to standard haemodynamics to determine flow XSA, SV and CO.

Figure 4:
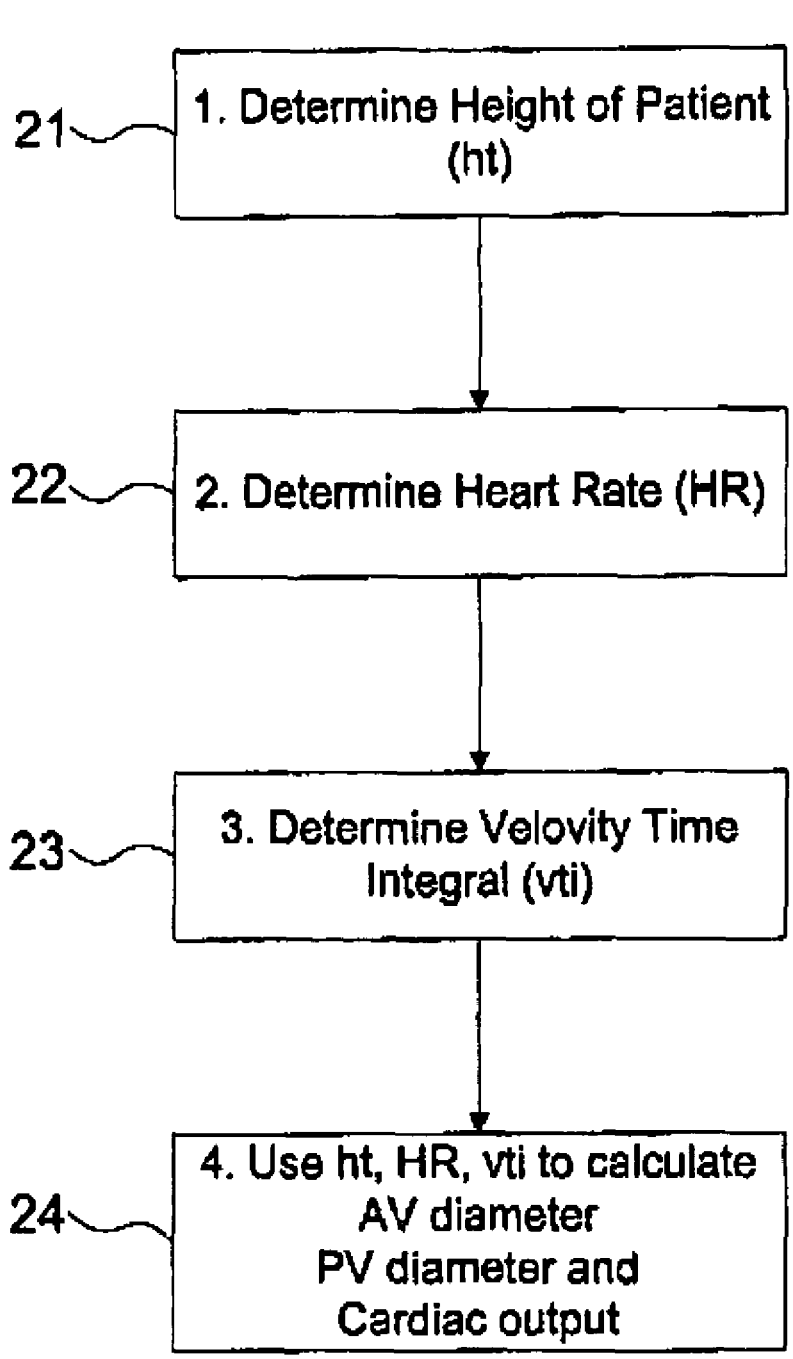
FIG. 4 illustrates a flow chart of the steps of the preferred embodiment.

FIG. 4 therefore illustrates a flowchart 20 of the steps involved in the preferred embodiment. Firstly, the height of the patient is determined at 21. Next, from the output screen dump of the transducer monitoring device, the heart rate is determined at 22 and the velocity time integral is measured at 23. These parameters are then utilised to calculate the corresponding AV and PV diameter which can then be utilised to calculate the cardiac output at 24.

In a first initial embodiment a measure for a population of individuals was studied and derived vti values of children and adults found in a sample population to be: Pvti=20.76±3.36 cm and Avti=23.38±3.38 cm, with a vti PV:AV ratio of 1:1.126.

Whilst the above values were used in calculations, obviously other population samples could be utilised.

Now the ratio of PV:AV was found to be 1.126. As CO=OT×HR×vti, and pulmonary flow equals systemic (aortic) flow in the absence of a shunt or significant regurgitation, then $$PV\ XSA \times HR \times PVvti = AV\ XSA \times HR \times AVvti$$

As $XSA=\pi r^2$ and AV diameter=(0.01×ht+0.25) and AV radius=(0.01×ht+0.25)/2 then $$(\pi \times (PVd/2)^2) \times 20.76 \times HR = (\pi \times ((0.01 \times ht+0.25)/2)^2) \times 23.38 \times HR$$

If HR PV=HR AV then $$(\pi \times (PVd/2)^2) \times 20.76 = (\pi \times ((0.01 \times ht+0.25)/2)^2) \times 23.38/20.76$$

$$(\pi \times (PVd/2)^2) = (\pi \times ((0.01 \times ht+0.25)/2)^2) \times 23.38/20.76$$

$$\pi \times (PVd/2)^2 = \pi \times ((0.01 \times ht+0.25)/2)^2 \times 1.126/\pi$$

$$(PVd/2)^2 = ((0.01 \times ht+0.25)/2)^2 \times 1.126$$

Taking the square root of both sides implies:

$$\sqrt{(PVd/2)^2} = \sqrt{((0.01 \times ht+0.25)/2)^2} \times \sqrt{1.126}$$

$$PVd/2 = (0.01 \times ht+0.25)/2 \times 1.06$$

$$PVd/2 = (0.01 \times ht+0.25) \times 1.06/2$$

Then PV Radius=PVd/2=(0.01×ht+0.25)×0.53=0.053×ht+ 0.1325 and PV diameter=PVd/2×2=(0.01×ht+0.25)× 1.06=0.0106×ht+0.265

Therefore both the aortic annular and the pulmonary annular diameter can be determined from simple height measurements as $$AVd = 0.01 \times ht + 0.25$$

and $$PVd = 0.0106 \times ht + 0.265$$

As a result, the above formulas can be utilised to calculate the cross-sectional area of the aortic and pulmonary valves. From this calculation, the stroke volume and CO can also be determined.

The flow cross sectional area, XSA, in $cm^2$ is required to calculate flow volumes and can be determined from direct 2D measurements or calculated from height referenced algorithms. From the above, the XSA algorithms are:

Aortic $$\text{As } AVd = 0.010 \times ht + 0.25$$

Pulmonary $$\text{As } PVd = 0.0106 \times ht + 0.265$$

then PV XSA=$\pi((0.0106 \times ht)+0.265)/2)^2$

Stroke Volume

Stroke volume, in $cm^3$, is the volume of blood ejected from the heart per beat and is equal to the cross sectional area times the flow vti. Therefore:

$$SV\ AV(\text{adult+children}) = \pi((0.010 \times ht+0.25)/2)^2 \times AVvti$$

$$SV\ PV(\text{adult+children}) = \pi((0.0106 \times ht+0.265)/2)^2 \times PVvti$$

Cardiac Output

Cardiac output, in liters per minute, is the volume of blood ejected from the heart per minute and is a function of the cross sectional area, the flow vti and the heart rate.

$$CO\ AV(\text{adult+children}) = \pi((0.010 \times ht+0.25)/2)^2 \times AVvti \times HR$$

$$CO\ PV(\text{adult+children}) = \pi((0.0106 \times ht+0.265)/2)^2 \times PVvti \times HR$$

By using the above formulas, a determination of important cardiac morphologic dimensions can be made from a subject height measurement. This measurement provides an alternative to the currently practiced direct measurement of these dimensions using complex imaging. This can allow for stand alone Doppler instruments to determine accurate measures of cardiac function without the use of complex and expensive imaging devices. This results in an improved method of determining CO in echocardiographic practice.

The foregoing describes only preferred embodiments of the present invention. Modifications, obvious to those skilled in the art can be made there to without departing from the scope of the invention.

The claims defining the invention are as follows:

1. A method of determining the cardiac output of a patient, the method comprising the steps of:
    (a) measuring the patient's height;
    (b) measuring the patient's heart rate;
    (c) measuring the velocity time integral or stroke distance of blood flowing from the heart of the patient via the pulmonary valve;
    (d) calculating, using a single variable formula, the diameter of the pulmonary valve of the patient wherein the single variable is the patient's height, and thereby calculating the cross sectional area of the pulmonary valve;
    (e) calculating a value for the cardiac output of the patient as the product of the heart rate, the velocity time integral and the cross sectional area of the pulmonary valve; and
    f) measuring the correlation between the patient's height and of the diameter of the pulmonary valve for a population of individuals, wherein said correlation is determined through the utilization of a first ratio of the relative speed of the flow velocity through the pulmonary artery and the flow velocity through the aortic annulus, and a second ratio of the patient's height to the aortic annulus diameter.

2. A method as claimed in claim 1 wherein said population is selected having similar body characteristics to said patient.

3. A method as claimed in claim 1 wherein the single variable formula is:

pulmonary annular diameter=0.0106×height(cms)+ 0.265 cm

4. A method as claimed in claim 1 wherein the first ratio is substantially equal to 1.126.

5. A method as claimed in claim 1, wherein measuring the velocity time integral or stroke distance of blood flowing from the heart of the patient via the pulmonary valve is performed with an ultrasonic transducer device.

* * * * *